United States Patent
Chang et al.

(10) Patent No.: US 9,982,233 B2
(45) Date of Patent: May 29, 2018

(54) METHOD FOR PROMOTING GENERATION OF STEM CELL-DERIVED EXOSOME BY USING THROMBIN

(71) Applicant: SAMSUNG LIFE PUBLIC WELFARE FOUNDATION, Seoul (KR)

(72) Inventors: Yun Sil Chang, Seoul (KR); Won Soon Park, Seoul (KR); Dong Kyung Sung, Seoul (KR); So Yoon Ahn, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 90 days.

(21) Appl. No.: 15/103,726

(22) PCT Filed: Dec. 12, 2014

(86) PCT No.: PCT/KR2014/012291
§ 371 (c)(1),
(2) Date: Jun. 10, 2016

(87) PCT Pub. No.: WO2015/088288
PCT Pub. Date: Jun. 18, 2015

(65) Prior Publication Data
US 2016/0333317 A1    Nov. 17, 2016

(30) Foreign Application Priority Data

Dec. 12, 2013 (KR) .................. 10-2013-0154891

(51) Int. Cl.
*C12N 5/0775*    (2010.01)
*A61K 35/51*    (2015.01)
(Continued)

(52) U.S. Cl.
CPC .......... *C12N 5/0665* (2013.01); *A61K 9/0019* (2013.01); *A61K 35/28* (2013.01);
(Continued)

(58) Field of Classification Search
None
See application file for complete search history.

(56) References Cited

U.S. PATENT DOCUMENTS

| 2006/0258003 A1 | 11/2006 | Pinset ......................... 435/366 |
| 2010/0034803 A1 | 2/2010 | Senga et al. ............... 424/94.64 |
| 2013/0216505 A1 | 8/2013 | Patel .................... C12N 5/0682 |

FOREIGN PATENT DOCUMENTS

| JP | 2002-535665 | 10/2002 | .............. G01N 30/88 |
| JP | 2006-509516 | 3/2006 | .............. C12N 5/06 |

(Continued)

OTHER PUBLICATIONS

Japanese Office Action from corresponding Japanese Application No. 2016-539062 dated Apr. 25, 2017.
(Continued)

*Primary Examiner* — David W Berke-Schlessel
(74) *Attorney, Agent, or Firm* — Harness, Dickey & Pierce, P.L.C.

(57) ABSTRACT

The present invention relates to a method of promoting generation of exosomes from stem cell by using thrombin. The method according to the present invention has superior effects of promoting generation of stem cell-derived exosomes and thus exosomes can be more efficiently obtained thereby compared to conventionally known methods. In addition, the method can be useful for related research.

10 Claims, 7 Drawing Sheets

(51) Int. Cl.
A61K 35/28 (2015.01)
A61K 35/545 (2015.01)
A61K 9/00 (2006.01)

(52) U.S. Cl.
CPC ............ *A61K 35/51* (2013.01); *A61K 35/545* (2013.01); *C12N 2501/734* (2013.01)

(56) References Cited

FOREIGN PATENT DOCUMENTS

| JP | 2007-535947 | 12/2007 | ............... C12N 5/06 |
|----|----|----|----|
| KR | 10-2005-0088118 | 9/2005 | ............... C12N 5/06 |
| KR | 10-2008-0036594 | 4/2008 | ............... C12N 9/64 |
| KR | 10-2010-0116812 | 11/2010 | ............... C12N 5/07 |
| WO | WO-2007049096 A1 * | 5/2007 | ........... C12N 5/0692 |
| WO | WO 2012/125471 | 9/2012 | ............. A61K 35/28 |
| WO | WO 2013/039000 | 3/2013 | ............. A61K 35/12 |
| WO | WO 2013/102219 | 7/2013 | ............... C12N 5/073 |
| WO | WO 2013/150303 | 10/2013 | ........... A61K 31/711 |
| WO | WO 2014/013258 | 1/2014 | ........... A61K 31/711 |

OTHER PUBLICATIONS

Japanese Office Action from corresponding Japanese Application No. 2016-539061 dated Mar. 21, 2017.
Extended European Search Report from corresponding European Application No. 14869537.2 dated Apr. 21, 2017.
Extended European Search Report from corresponding European Application No. 14868825.2 dated Jul. 7, 2017.
Aharon A., et al.; "Microparticles, thrombosis and cancer", 2008 Elsevier Ltd.
Ruenn Chai Lai, et al.; "Mesenchymal stem cell exosome: a novel stem cell-based therapy for cardiovascular disease", Regen. Med., 2011, 6(4), 481-492.
Xin, H. et al.; "System administration of exosomes released from mesnchymal stromal cells promote functional recovery and neurovascular plasticity after stroke in rats", Journal of Cerebral Blood Flow & Metabolism (2013) 33, 1711-1715.
Ahn, Sy et al.; "Mesenchymal Stem Cells Prevent Hydrocephalus After Severe Intraventricular Hemmorage", Stroke, 2013, Vo. 44, pp. 497-504.
International Search Report (ISR) dated Mar. 25, 2015 in PCT/KR2014/012291 published as WO 2015/088288 with English Translation.
Chen T. S., et al. (2011). "Enabling a robust scalable manufacturing process for therapeutic exosomes through oncogenic immortalization of human esc-derived MSCs" *J. Transl. Med.*, 9(47):1-10.
Vogl, M. et al., (2013). "Can thrombin-activated platelet releasate compensate the age-induced decrease in cell proliferation of MSC?" *Journal of Orthopaedic Research*, 31(11):1786-1795.

* cited by examiner

METHOD FOR PROMOTING GENERATION OF STEM CELL-DERIVED EXOSOME BY USING THROMBIN

CROSS-REFERENCE TO RELATED APPLICATIONS

This application is a national phase application of PCT Application No. PCT/KR2014/012291, filed on Dec. 12, 2014, which claims the benefit and priority to Korean Patent Application No. 10-2013-0154891, filed Dec. 12, 2013. The entire disclosures of the applications identified in this paragraph are incorporated herein by references.

FIELD

The present invention relates to a method of promoting generation of exosomes from stem cell by using thrombin

BACKGROUND

An exosome is a small vesicle with a membrane structure secreted from a variety of cell types. Exosomes reportedly have a diameter of about 30-100 nm. It was observed that exosomes were derived from specific intracellular parts called multivesicular bodies (MVBs) and released and secreted to the outside of cells, instead of being directly detached and released from plasma membranes, by means of an electron microscope. That is, when fusion between multivesicular bodies and plasma membranes occurs, vesicles are released to the outside of cells. These vesicles are called exosomes. Although a molecular mechanism for a formation process of such exosomes is not clearly determined, it is known that a variety of immunocytes including B lymphocytes, T lymphocytes, dendritic cells, platelets, macrophages, etc., tumor cells, and stem cells, as well as red blood cells, produce and secret exosomes during their lifespan. In particular, it is known that, since exosomes derived from stem cells contain nuclear components as well as receptors and proteins, exosomes play important roles in intercellular communication. In addition, since exosomes contain a relatively small amount of animal serum, compared to stem cells, the risk of symptoms (zoonosis) due to infection caused by animal serum can also be eliminated. Considering such characteristics of exosomes, it is anticipated that cytotherapy using exosomes can be a new paradigm to overcome the limitations of existing stem cell therapies.

DISCLOSURE

Technical Problem

Accordingly, the present inventors continued research on a method of increasing production efficiency of the aforementioned highly usable exosomes. As a result, the present inventors confirmed that generation of stem cell-derived exosomes is promoted by using thrombin, thus completing the present invention.

Accordingly, it is an object of the present invention to provide a method of promoting generation of stem cell-derived exosomes using thrombin.

It is another object of the present invention to provide a medium composition for promoting generation of the stem cell-derived exosomes, the medium composition including thrombin.

It is still another object of the present invention to provide a method for increasing expression of growth factors in the stem cell-derived exosomes using thrombin.

Technical Solution

One aspect of the present invention provides a method of promoting generation of stem cell-derived exosomes, the method including a step of culturing stem cells in a medium including thrombin.

Another aspect of the present invention provides a medium composition for promoting generation of the stem cell-derived exosomes, the medium composition including thrombin.

Still another aspect of the present invention provides a method of increasing expression of growth factors in the stem cell-derived exosome, the method including a step of culturing the stem cells in the medium including thrombin.

Advantageous Effects

The method according to the present invention has superior effects of promoting generation of stem cell-derived exosomes and thus exosomes can be more efficiently obtained thereby compared to conventionally known methods. In addition, the method can be useful for related research.

MODES OF THE INVENTION

Hereinafter, the present invention will be described in detail.

The present invention provides a method of promoting generation of stem cell-derived exosomes, the method including a step of culturing the stem cells in a medium including thrombin.

The thrombin may be included at a concentration of 1 to 1000 U/ml, preferably, a concentration of 10 to 200 U/ml, in the medium.

Culturing duration is not limited so long as exosomes can be generated. Preferably, culturing may be carried out for 12 to 48 hours.

In the present invention, "stem cells" refers to undifferentiated cells having the ability to differentiate into two or more different cell types.

The stem cells of the present invention may be autologous or allogeneic stem cells and may be derived from any animal including humans and non-human mammals. In addition, the stem cells may be derived from, without being limited to, adults or embryos. The stem cells of the present invention include embryonic stem cells or adult stem cells, preferably, adult stem cells. The adult stem cells may be, without being limited to, mesenchymal stem cells, human tissue-derived mesenchymal stromal cells (mesenchymal stromal cell), human tissue-derived mesenchymal stem cells, multipotent stem cells, or amniotic epithelial cells, preferably, mesenchymal stem cells. The mesenchymal stem cells may be derived from, without being limited to, the umbilical cord, umbilical cord blood, bone marrow, fat, muscle, nerve, skin, amnion, placenta, etc.

In the present invention, "medium" refers to a composition including essential ingredients required for growth and proliferation of cells cultured in vitro. Examples of the medium include all media for culturing stem cells generally used in the art. The medium may be, for example, a commercially available medium, such as Dulbecco's Modified Eagle's Medium (DMEM), Minimal Essential Medium (MEM), Basal Medium Eagle (BME), RPMI 1640, Dulbecco's Modified Eagle's Medium: Nutrient Mixture F-10 (DMEM/F-10), Dulbecco's Modified Eagle's Medium/Nutrient Mixture F-12 (DMEM/F-12), α-Minimal essential Medium (α-MEM), Glasgow's Minimal Essential Medium (G-MEM), Isocove's Modified Dulbecco's Medium (IMDM), or KnockOut DMEM or an artificially synthesized medium, but the present invention is not limited thereto. The medium of the present invention generally includes a carbon source, a nitrogen source, and trace elements and may further include amino acids, an antibiotic, etc.

In a specific example of the present invention, mesenchymal stem cells were treated with a serum-free-culture medium (MEM alpha media) containing thrombin at 10 to 100 U/ml and then cultured for 24 hours to promote generation of stem cell-derived exosomes. Generated stem cell-derived exosomes were isolated by ultracentrifugation.

The method according to the present invention has superior effects of promoting the generation of stem cell-derived exosomes and thus exosomes can be more efficiently obtained thereby compared to conventionally known methods.

In addition, the present invention provides a medium composition for promoting the generation of the stem cell-derived exosomes, the medium composition including thrombin.

Here, thrombin may be included at a concentration of 1 to 1000 U/ml in the medium. Preferably, thrombin may be included at a concentration of 10 to 200 U/ml.

The medium composition of the present invention may further include, other than thrombin, one or more publicly known exosome generation promotion substances, but the present invention is not limited thereto.

In addition, the present invention provides a method of increasing expression of growth factors in the stem cell-derived exosomes, the method including a step of culturing the stem cells in the medium including thrombin.

In the present invention, "growth factors" refer to proteinous bioactive substances promoting cell division or growth, and differentiation thereof. Examples of the growth factors include brain-derived neurotropic factor (BDNF), fibroblast growth factor (FGF), hepatocyte growth factor (HGF), nerve growth factor (NGF), vascular endothelial growth factor (VEGF), insulin-like growth factor (IGF), transforming growth factor (TGF), platelet-derived growth factor (PDGF), bone-derived growth factor (BDF), colony stimulation factor (CSF), epidermal growth factor (EGF), keratinocyte growth factor (KGF), etc.

Preferred examples of the growth factors include brain-derived neurotropic factor (BDNF), fibroblast growth factor (FGF), hepatocyte growth factor (HGF), nerve growth factor (NGF), or vascular endothelial growth factor (VEGF), but the present invention is not limited thereto.

Hereinafter, the present invention will be described in more detail with reference to the following preferred examples. However, it should be understand that the following examples serve merely to concretely explain the spirit of the invention and therefore, there is no intent to limit the invention to the examples.

Example 1. Isolation of Stem Cell-Derived Exosomes

To isolate stem cell-derived exosomes, thrombin and ultracentrifugation were used. More particularly, $1 \times 10^6$ of cord blood-derived mesenchymal stem cells were aliquoted into 60 mm culture plates (Orange Scientific cat#4450200) and then cultured for one week. When the cells were cultured to confluence in the culture plate, a medium thereof was changed with a new serum-free culture medium including thrombin at each concentration (10, 20, 50, or 100 U/ml) in the medium, followed by culturing for 24 hours. Subsequently, the culture medium was aliquoted into centrifugation tubes, followed by centrifuging at 4° C. and 10,000 rpm for 30 minutes. Supernatants were transferred to new tubes to remove cell debris. The supernatants were again ultracentrifuged at 4° C. and 100,000 rpm for two hours. Supernatants were removed and exosomes were isolated (final concentration: 15 µg/ml).

Example 2. Identification of Stem Cell-Derived Exosomes

To determine whether exosomes isolated according the process of Example 1 had publicly known intrinsic exosome characteristics, the following experiments were conducted. First, the isolated exosomes were observed by SEM imaging. Expression of CD63 and CD9 (System Bioscience, Mountain View, Calif., USA), as exosome markers, was investigated by Western blotting. In addition, exosome membranes were lysed with a lysis buffer and then proteins in exosomes were isolated. The amounts of HGF and VEGF, as growth factors, in the exosomes were measured using a Procarta immunoassay kit (Affymetrix, Santa Clara, Calif., USA). Results are respectively illustrated in FIGS. 1 to 3.

Figure 1:
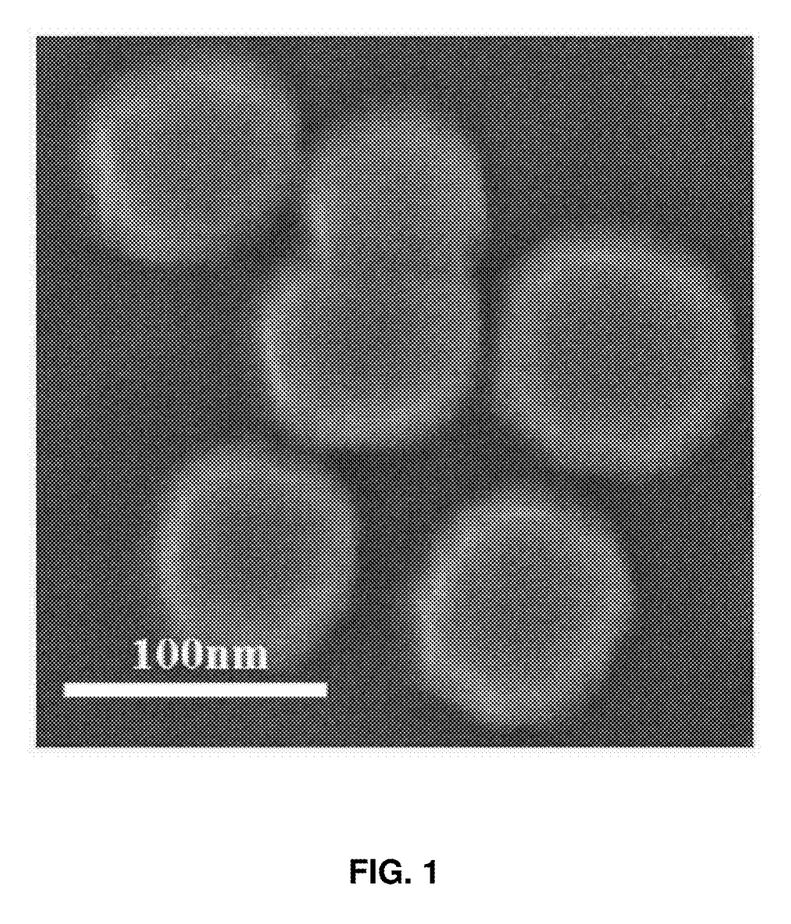
FIG. 1 illustrates the shapes of stem cell-derived exosomes obtained according to a method of the present invention, confirmed by SEM image analysis.

As illustrated in FIG. 1, it can be confirmed that the exosomes isolated according to Example 1 have normal globular shapes having a diameter of about 100 nm.

Figure 2:
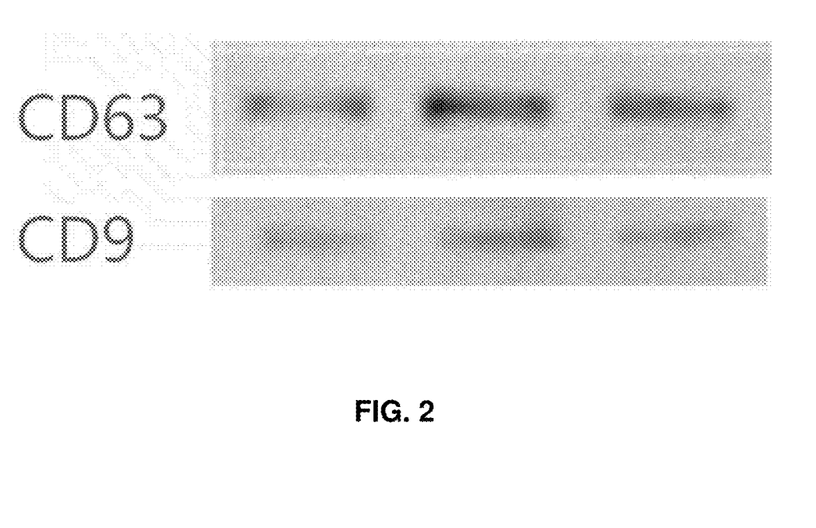
FIG. 2 illustrates expression of CD63 and CD9, as exosome markers, in stem cell-derived exosomes obtained by the method according to the present invention.
Figure 3:
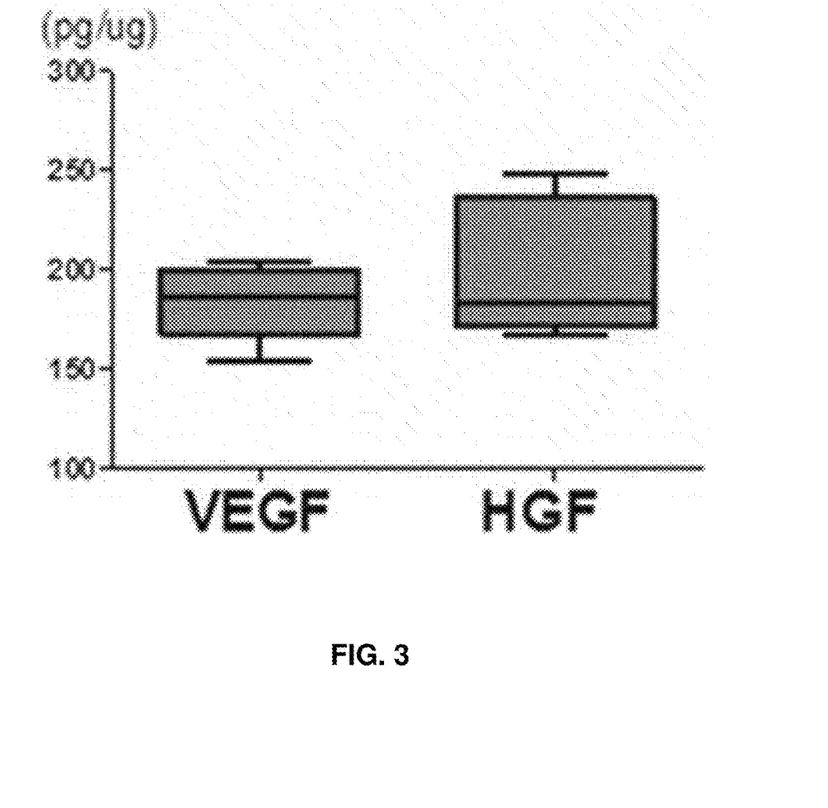
FIG. 3 illustrates expression of VEGF and HGF, as growth factors, in stem cell-derived exosomes obtained by the method according to the present invention.

In addition, as illustrated in FIGS. 2 and 3, it can be confirmed that the exosomes isolated according to Example 1 normally express CD63 and CD9, as exosome markers, and VEGF and HGF, as growth factors, present in the exosomes.

Example 3. Exosome Generation Promotion Effect According to Thrombin Treatment 3-1. Investigation of Exosome Generation Degrees Dependent Upon Thrombin Treatment Concentrations To investigate the stem cell-derived exosome generation degrees dependent upon thrombin treatment concentrations, exosomes were isolated in the same manner as in Example 1, treated with varying thrombin concentrations during stem cell culturing, and quantified. Results are illustrated in FIG. 4.

Figure 4:
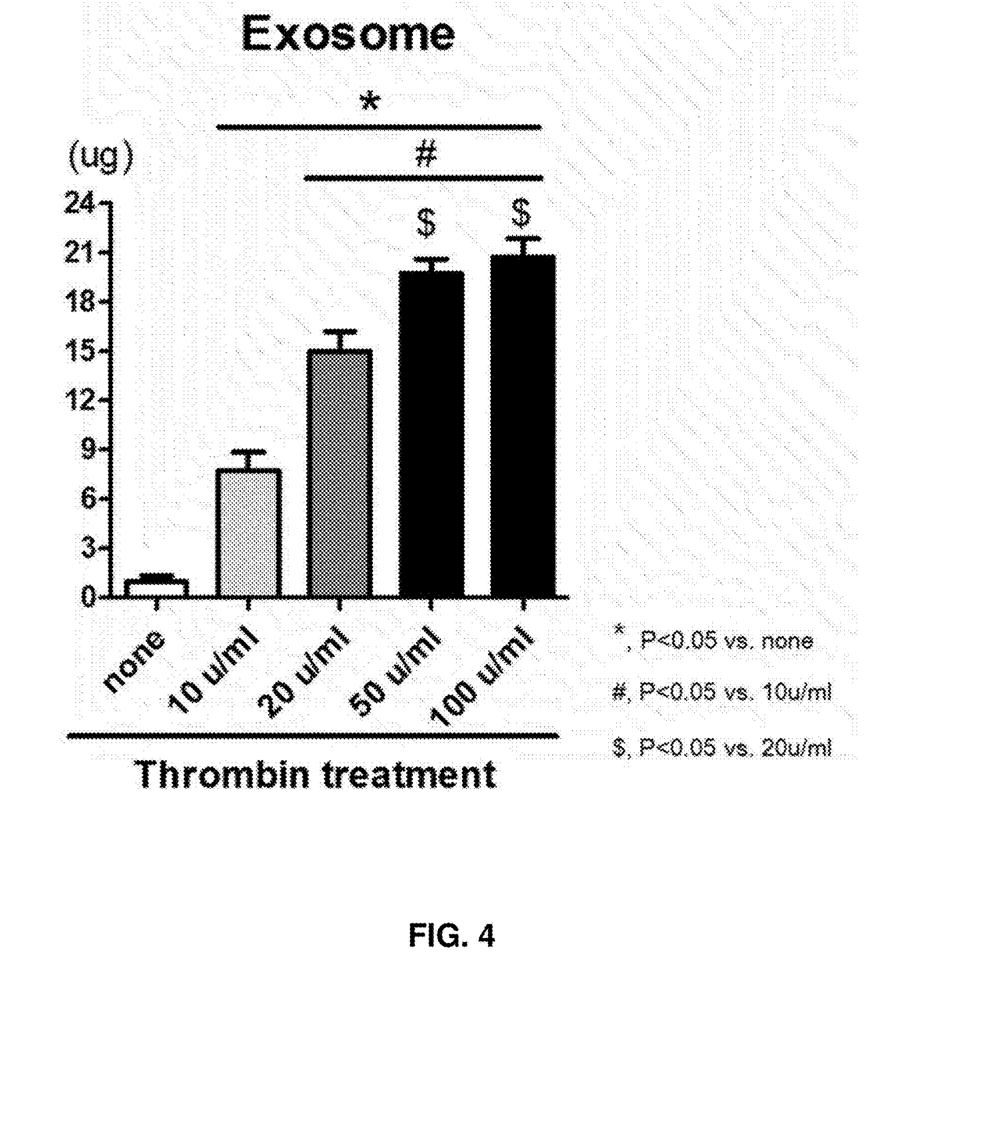
FIG. 4 illustrates the generation degrees of stem cell-derived exosomes, dependent upon thrombin treatment concentrations.

As illustrated in FIG. 4, it can be confirmed that, with increasing thrombin treatment concentrations, generation of stem cell-derived exosomes is significantly promoted.

3-2. Verification of Efficiency of Exosome Generation Promotion Method Using Thrombin To verify the efficiency of the exosome generation promotion method using thrombin, exosomes were isolated in the same manner as in Example 1, except that a culture medium was treated with LPS or $H_2O_2$ instead of thrombin and quantified. Results are illustrated in FIG. 5.

Figure 5:
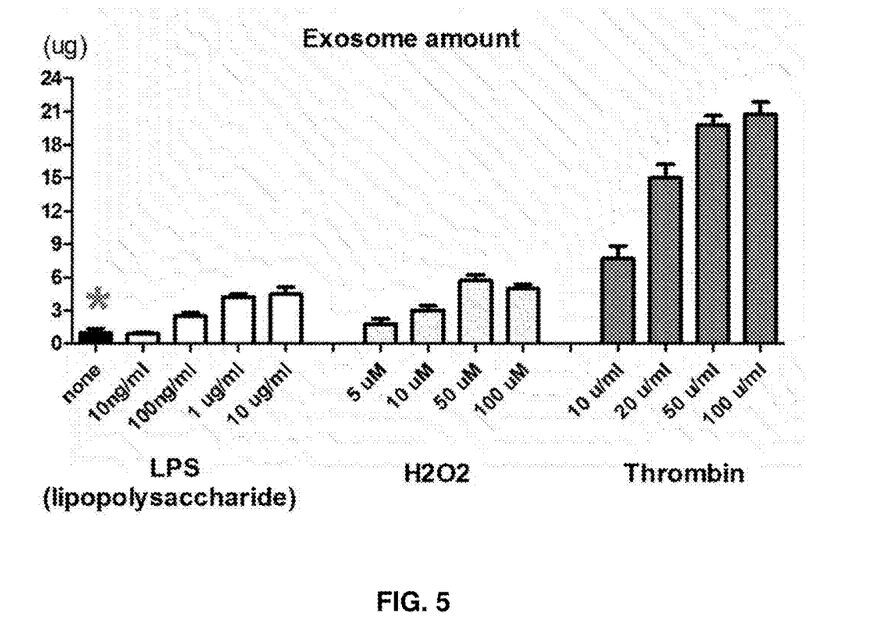
FIG. 5 illustrates the generation degrees of stem cell-derived exosome, dependent upon treatment concentrations of LPS, $H_2O_2$, or thrombin.

As illustrated in FIG. 5, when stem cells are treated with thrombin during culturing thereof, generation of the stem cell-derived exosomes remarkably increases, compared to groups treated with other substances.

3-3. Observation of Endoplasmic Reticulum Formation in Stem Cells According to Thrombin Treatment To investigate whether thrombin treatment affects endoplasmic reticulum formation in stem cells, umbilical cord blood-derived mesenchymal stem cells were cultured in a serum-free-culture medium (MEM alpha media) containing thrombin at 50 U/ml for six hours. Subsequently, exosomes were isolated in the same manner as in Example 1 and observed by means of an electron microscope. Results are illustrated in FIG. 6.

Figure 6:
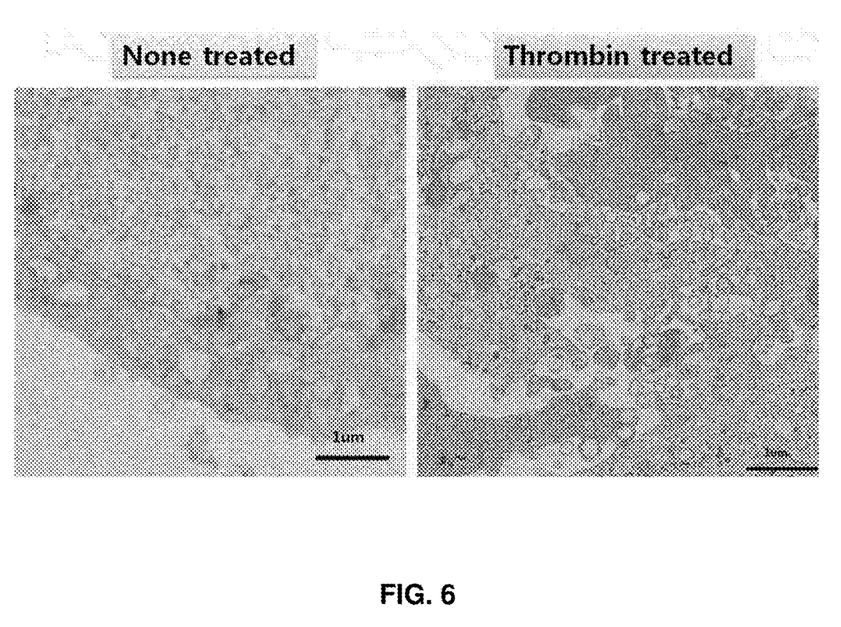
FIG. 6 illustrates a formation degree of endoplasmic reticulums in stem cells according to thrombin treatment.

As illustrated in FIG. 6, it can be confirmed that, by thrombin treatment, endoplasmic reticulum formation in stem cells is increased and exosome secretion is induced.

3-4. Observation of Expressions of Growth Factors in Exosomes Due to Thrombin Treatment To investigate whether expression of growth factors in exosomes is affected by thrombin treatment, umbilical cord blood-derived mesenchymal stem cells were cultured in a serum-free-culture medium (MEM alpha media) containing 50 U/ml of thrombin for six hours. Subsequently, exosomes were isolated in the same manner as in Example 1. Membranes of the exosomes were lysed with a lysis buffer and then proteins in the exosomes were isolated. The amounts of BDNF, FGF, HGF, NGF, IL-6, and VEGF, as growth factors, in the exosomes were measured using a Procarta immunoassay kit (Affymetrix, Santa Clara, Calif., USA). Results are illustrated in FIG. 7.

Figure 7:
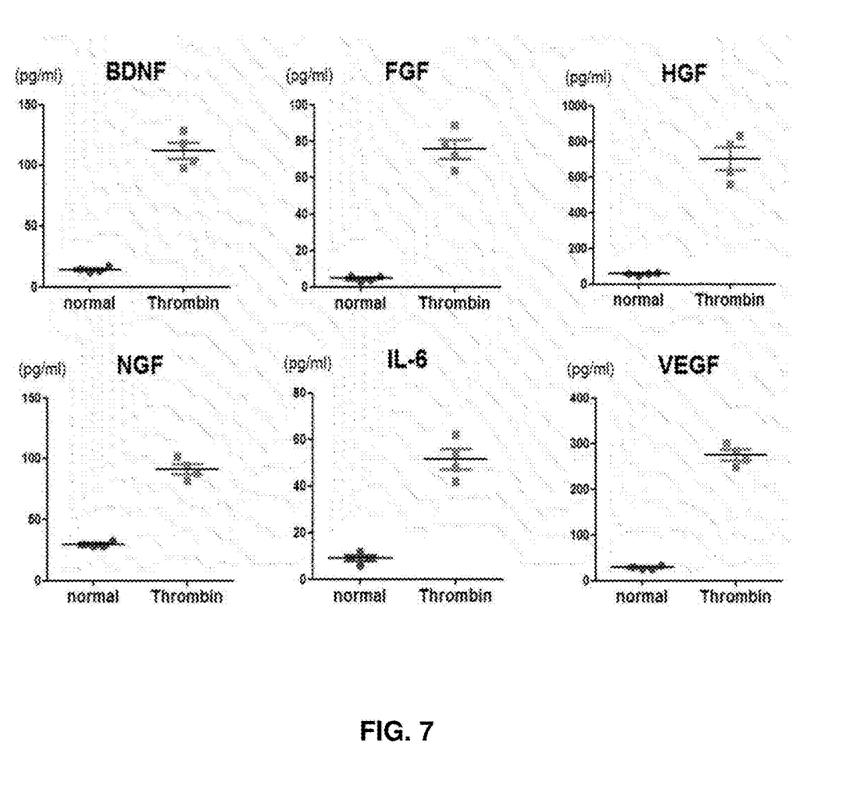
FIG. 7 illustrates results of measurement of expression of growth factors in exosomes dependent upon thrombin treatment.

As illustrated in FIG. 7, it can be confirmed that expressions of BDNF, FGF, HGF, NGF, IL-6, and VEGF, as growth factors, in the exosomes are increased by thrombin treatment.

From the aforementioned results, it can be confirmed that, by using thrombin, generation of the stem cell-derived exosomes can be promoted and expression of the growth factors in the exosomes can be increased.

INDUSTRIAL APPLICABILITY

The method according to the present invention has superior effects of promoting generation of stem cell-derived exosomes and thus exosomes can be more efficiently obtained thereby compared to conventionally known methods. In addition, the method can be useful for related research.

What is claimed is:

1. A method of enhancing an amount of stem-cell derived exosome per stem cell, the method comprising:
    culturing a stem cell in a medium comprising thrombin.

2. The method according to claim 1, wherein the stem cell is an embryonic stem cell or an adult stem cell.

3. The method according to claim 2, wherein the adult stem cell comprises one or more adult stem cell types selected from the group consisting of mesenchymal stem cell, human tissue-derived mesenchymal stromal cell, human tissue-derived mesenchymal stem cell, multipotent stem cell, and amniotic epithelial cell.

4. The method according to claim 3, wherein the mesenchymal stem cells are derived from one or more tissues selected from the group consisting of umbilical umbilical cord, umbilical cord blood, bone marrow, fat, muscle, nerve, skin, amnion, and placenta.

5. The method according to claim 1, wherein the medium comprises one or more selected from the group consisting of Dulbecco's Modified Eagle's Medium (DMEM), Minimal Essential Medium (MEM), Basal Medium Eagle (BME), RPMI 1640, Dulbecco's Modified Eagle's Medium/Nutrient Mixture F-10 (DMEM/F-10), Dulbecco's Modified Eagle's Medium/Nutrient Mixture F-12 (DMEM/F-12), α-Minimal essential Medium (α-MEM), Glasgow's Minimal Essential Medium (G-MEM), Isocove's Modified Dulbecco's Medium (IMDM), and KnockOut DMEM.

6. The method according to claim 1, wherein the medium comprises the thrombin at a concentration of 1 to 1000 U/ml.

7. The method according to claim 1, wherein the culturing is performed for 12 to 48 hours.

8. A method of increasing expression of a growth factor in an exosome derived from a stem cell, the method comprising:
    culturing a stem cell in a medium comprising thrombin.

9. The method according to claim 8, wherein the growth factor comprises one or more selected from the group consisting of brain-derived neurotropic factor (BDNF), fibroblast growth factor (FGF), hepatocyte growth factor (HGF), nerve growth factor (NGF), and vascular endothelial growth factor (VEGF).

10. A method for enhancing an amount of stem-cell derived exosome per stem cell comprising:
    providing a medium composition comprising thrombin for exosome generation;
    culturing stem cells in said medium.

* * * * *